(12) United States Patent
Ernst et al.

(10) Patent No.: US 8,383,679 B2
(45) Date of Patent: Feb. 26, 2013

(54) CRYSTAL FORM OF CALCIUM 3-ACETYLAMINOPROPANE-1-SULFONATE

(75) Inventors: Antje Ernst, Darmstadt (DE); Clemens Kuehn, Darmstadt (DE); Matthias Bartels, Darmstadt (DE); Christoph Saal, Otzberg (DE); Nathalie Bosc, Montanay (FR)

(73) Assignee: Merck Patent Gesellschaft mit beschränkter Haftung, Darmstadt (DE)

( * ) Notice: Subject to any disclaimer, the term of this patent is extended or adjusted under 35 U.S.C. 154(b) by 50 days.

(21) Appl. No.: 13/120,577

(22) PCT Filed: Aug. 25, 2009

(86) PCT No.: PCT/EP2009/006150
§ 371 (c)(1),
(2), (4) Date: Mar. 23, 2011

(87) PCT Pub. No.: WO2010/034384
PCT Pub. Date: Apr. 1, 2010

(65) Prior Publication Data
US 2011/0196041 A1    Aug. 11, 2011

(30) Foreign Application Priority Data

Sep. 24, 2008 (DE) .......................... 10 2008 048 791

(51) Int. Cl.
*A01N 37/00* (2006.01)
*A61K 31/185* (2006.01)
(52) U.S. Cl. ......... 514/553; 514/578; 514/562; 514/105
(58) Field of Classification Search .................. 514/553, 514/578; 562/105
See application file for complete search history.

(56) References Cited

U.S. PATENT DOCUMENTS 4,355,043 A * 10/1982 Durlach ........................ 514/494
6,265,437 B1 * 7/2001 Berthelon et al. ............. 514/474

FOREIGN PATENT DOCUMENTS

| CN | 101 492 400 A | 7/2009 |
| GB | 2 051 789 A | 1/1981 |
| KR | 2008-0097716 A | 11/2008 |

OTHER PUBLICATIONS

Toffoli et al, Aeta Cryst. (1188) C44, 1493-1494.*
News Watch, Drug for alcoholism is effective against tinnitus, 2005.*
International Search Report of PCT/EP2009/006150 (Oct. 21, 2009).

* cited by examiner

*Primary Examiner* — Brandon Fetterolf
*Assistant Examiner* — Jean Cornet
(74) *Attorney, Agent, or Firm* — Millen, White, Zelano & Branigan, P.C.

(57) ABSTRACT

The present invention relates to a novel crystal form of calcium 3-acetylaminopropane-1-sulfonate, to a process for the preparation thereof, and to the use thereof in medicaments.

18 Claims, 7 Drawing Sheets

Fig. 1: X-ray powder diffraction pattern of crystal form I of calcium 3-acetylaminopropane-1-sulfonate Fig. 2: X-ray powder diffraction pattern of crystal form II of calcium 3-acetylaminopropane-1-sulfonate Fig. 3: Individual crystal structure of calcium 3-acetylaminopropane-1-sulfonate; left: view along the a axis; right: view along the c axis Fig. 4: FT-IR spectrum of form II of calcium 3-acetylaminopropane-1-sulfonate Fig. 5: FT-Raman spectrum of form II of calcium 3-acetylaminopropane-1-sulfonate Fig. 6: FT-IR spectrum of form I of calcium 3-acetylaminopropane-1-sulfonate Fig. 7: FT-Raman spectrum of form I of calcium 3-acetylaminopropane-1-sulfonate

CRYSTAL FORM OF CALCIUM 3-ACETYLAMINOPROPANE-1-SULFONATE

The present invention relates to a novel crystal form of calcium 3-acetylaminopropane-1-sulfonate, to a process for the preparation thereof, and to the use thereof in medicaments.

Calcium 3-acetylaminopropane-1-sulfonate, which is also referred to as "active compound" below, has the following chemical structure Calcium 3-acetylaminopropane-1-sulfonate was described for the first time in DE 3019350 A1 and is employed as active compound for the treatment of alcoholism. The use of this active compound for the treatment of tinnitus is likewise described.

According to DE 3019350 A1, calcium 3-acetylaminopropane-1-sulfonate is a crystalline colourless powder having a solidification point of approximately 270° C. and a water content of 3.6%, as elemental composition 9.7% of calcium and 6.8% of nitrogen were measured (the theoretical values are 10% and 7%).

Toffoli et al. describes the crystal form of calcium 3-acetylaminopropane-1-sulfonate (P. Toffoli, N. Rodier, R. Ceolin, P. Ladure, G. Tran, Acta Crystal-lographica, Sect. C, Crystal Structure Communications, 1988, 44, 1493) this form is also referred to as "crystal form I" or "form I" below. According to Toffoli et. al., form I is characterised by the following parameters: mono-clinic, $P2_1/c$, a=5.4584 Å, b=18.949 Å, c=8.550 Å, β=105.49°, V=852.2 Å$^3$.

The crystal form of calcium 3-acetylaminopropane-1-sulfonate described in Toffoli et al. corresponds to the crystal form of calcium 3-acetylaminopropane-1-sulfonate as present in the marketed medicament.

It has now been found that calcium 3-acetylaminopropane-1-sulfonate can also exist in another crystal form, which is also called "form II" or "crystal form II" below. The solidification point of form II is approximately 364° C. and is thus significantly higher than described in DE 3019350 A1.

Surprisingly, it has been found for novel found form II that it is thermodynamically more stable than form I.

The dissolution rate of active compounds is determined, inter alia, by their crystal form. If an active compound exists in various crystal forms and if it is intended as active compound for a medicament, it is advantageous for the thermodynamically more stable form of the active compound to be used. This is because it can thus basically be excluded that the thermodynamically less stable (metastable) form present in the medicament converts into the thermodynamically more stable form after preparation of the medicament until it is used by the patient, in particular during storage of the medicament.

Conversion from one crystal form into another results, inter alia, in a change in the dissolution rate of the active compound, meaning that the original release of the active compound from the medicament is no longer reproducible. A change in the dissolution rate of the active compound disadvantageously has the consequence that, after the medicament has been taken by the patient, the active compound present therein is no longer released from the medicament and absorbed in the pre-determined rate and amount in the gastrointestinal tract, meaning that its bioavailability and thus also its efficacy is no longer guaranteed. The use of the medicament comprising the active compound is thus overall placed in doubt.

While the active compound according to DE 3019350 A1 contains water of crystallisation (3.6% is quoted), this is not present in form II.

As already mentioned, crystal form II of the active compound is thermodynamically more stable than its crystal form I. Thus, in suspension-conversion experiments with crystal form I, rearrangement to crystal form II arises. Furthermore, significantly lower enthalpies of solution arise for form II with 16.2±0.2 J/g compared with −23.1±0.2 J/g for form I ((6.9±0.4 J/g), in each case measured in water at 25° C. using a 2225 Thermometrics Solution calorimeter). Form II thus has a lower free Gibbs enthalpy and is thermodynamically more stable than form I.

Form II can be prepared by stirring a suspension of crystals of form I of calcium 3-acetylaminopropane-1-sulfonate in a suitable suspension medium and separating off and drying the residue obtained. Suitable suspension media are solvents in which the active compound is soluble, where the active compound is employed in a weight ratio in relation to the respective solvent in the suspension in which the solubility limit of the active compound in the solvent is exceeded, so that the active compound is predominantly in the form of a solid in the suspension. Suitable suspension media are, for example, water, methanol and/or tetrahydrofuran (THF), where water is particularly preferred.

Form I of the active compound can be obtained by the process described in the prior art.

The crystal forms can be determined by standard methods, as described, for example, in C. W. Bunn, "Chemical Crystallography" 1948, Clarendon Press, London; or H. P. Klug, L. E. Alexander, "X-Ray Diffraction Procedures" 1974, John Wiley and Sons, New York.

BRIEF DESCRIPTION OF THE DRAWINGS

Figure 1:
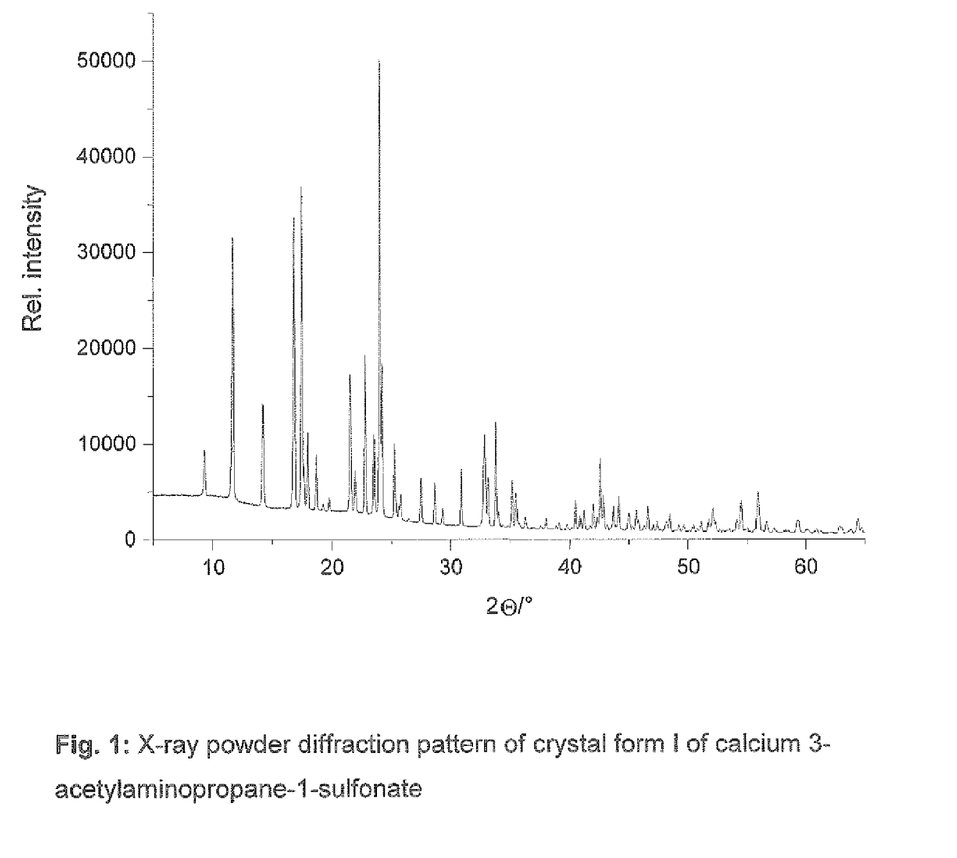
FIG. 1 shows an X-ray diffraction pattern of form I of calcium 3-acetyl-aminopropane-1-sulfonate.

FIG. 1 shows an X-ray diffraction pattern of form I of the material, the parameters arising from this are shown in Table I below.

TABLE 1

X-ray diffraction pattern of form I, measured using a Bruker D5000 diffractometer, transmission mode, generator power 40 kV/30 mA, Cu—Kα1 radiation (λ = 1.54 Å), position-sensitive detector (3.3 kV), measurement range: 3-65° 2Θ, step size: 0.05° 2Θ, time/step: 1.4 s. The diffraction patterns are background-corrected throughout the recording range 3-65° 2Θ, and the reflection intensities of the strongest reflections are determined. The tolerance of the angle positions is ±0.1° 2Θ for the Cu—Kα1 radiation used.

| No. | d [Å] | 2Θ ± 0.1 | I/I$_0$ [%] |
|---|---|---|---|
| 1 | 9.34 | 9.3 | 18 |
| 2 | 7.61 | 11.7 | 62 |
| 3 | 6.21 | 14.2 | 27 |
| 4 | 5.30 | 16.8 | 66 |

TABLE 1-continued

X-ray diffraction pattern of form I, measured using a Bruker D5000 diffractometer, transmission mode, generator power 40 kV/30 mA, Cu—Kα1 radiation (λ = 1.54 Å), position-sensitive detector (3.3 kV), measurement range: 3-65° 2Θ, step size: 0.05° 2Θ, time/step: 1.4 s. The diffraction patterns are background-corrected throughout the recording range 3-65° 2Θ, and the reflection intensities of the strongest reflections are determined. The tolerance of the angle positions is ±0.1° 2Θ for the Cu—Kα1 radiation used.

| No. | d [Å] | 2Θ ± 0.1 | I/I₀ [%] |
|---|---|---|---|
| 5 | 5.08 | 17.5 | 71 |
| 6 | 4.93 | 18.0 | 22 |
| 7 | 4.76 | 18.7 | 18 |
| 8 | 4.49 | 19.7 | 10 |
| 9 | 4.13 | 21.6 | 34 |
| 10 | 4.06 | 21.9 | 14 |
| 11 | 3.91 | 22.7 | 38 |
| 12 | 3.77 | 23.6 | 21 |
| 13 | 3.69 | 24.0 | 100 |
| 14 | 3.53 | 25.2 | 20 |

Figure 2:
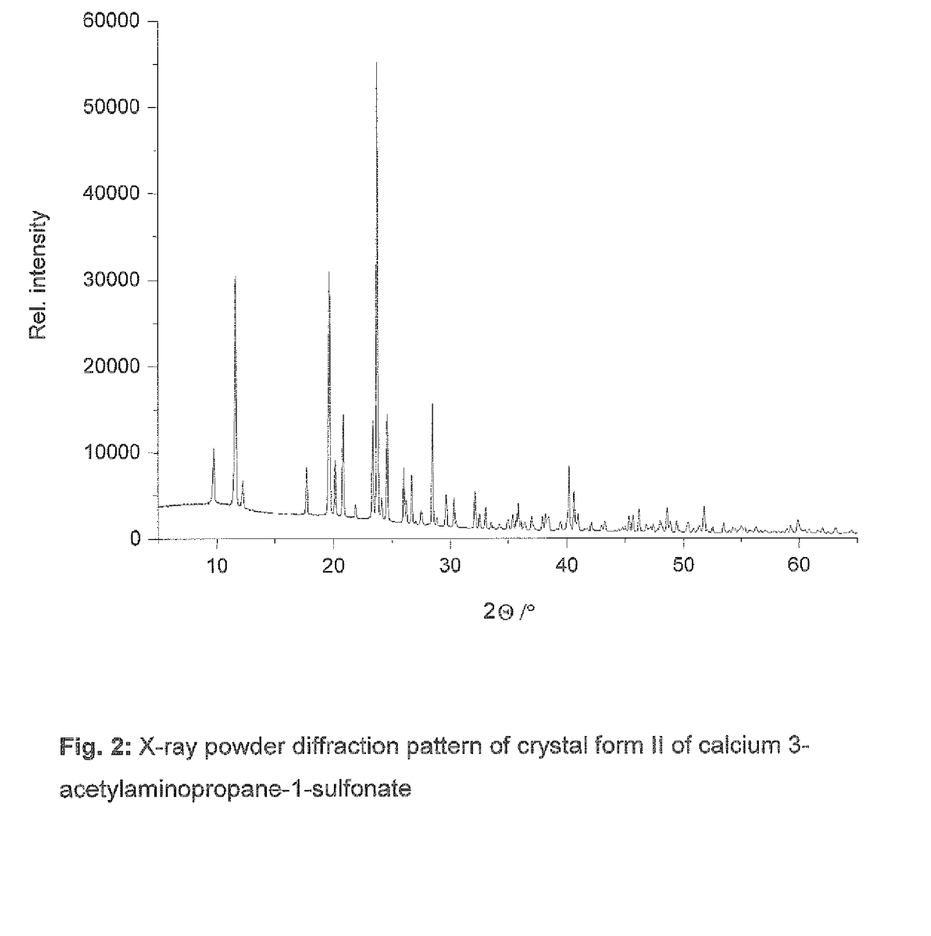
FIG. 2 shows an X-ray diffraction pattern of form II of calcium 3-acetyl-aminopropane-1-sulfonate.

FIG. 2 shows an X-ray diffraction pattern of form II of the active compound, the parameters arising from this are compiled in Table 2 below.

TABLE 2

X-ray diffraction pattern of form II, measurement and evaluation is carried out as described for Table 1.

| No. | d [Å] | 2Θ ± 0.1 | I/I₀ [%] |
|---|---|---|---|
| 1 | 7.59 | 11.6 | 55 |
| 2 | 4.51 | 19.7 | 56 |
| 3 | 4.26 | 20.8 | 26 |
| 4 | 3.80 | 23.4 | 25 |
| 5 | 3.74 | 23.8 | 100 |
| 6 | 3.61 | 24.6 | 26 |
| 7 | 3.13 | 28.5 | 28 |

In a preferred embodiment, form II is characterised by X-ray data in accordance with Table 2a below. The data in accordance with Table 2a contain the reflections from Table 2 and in addition 6 further reflections of lower intensity.

TABLE 2a

X-ray diffraction pattern of form II, measurement and evaluation is carried out as described for Table 1.

| No. | d [Å] | 2Θ ± 0.1 | I/I₀[%] |
|---|---|---|---|
| 1 | 9.04 | 9.8 | 19 |
| 2 | 7.59 | 11.6 | 55 |
| 3 | 5.01 | 17.7 | 15 |
| 4 | 4.51 | 19.7 | 56 |
| 5 | 4.40 | 20.2 | 17 |
| 6 | 4.26 | 20.8 | 26 |
| 7 | 3.80 | 23.4 | 25 |
| 8 | 3.74 | 23.8 | 100 |
| 9 | 3.61 | 24.6 | 26 |
| 10 | 3.42 | 26.0 | 15 |
| 11 | 3.33 | 26.7 | 13 |
| 12 | 3.13 | 28.5 | 28 |
| 13 | 2.24 | 40.2 | 15 |

The present invention therefore relates to crystal form II of calcium 3-acetyl-aminopropane-1-sulfonate, characterised by the characteristic lattice-plane separations indicated in Table 2.

The present invention likewise relates to crystal form II of calcium 3-acetyl-aminopropane-1-sulfonate, characterised by the characteristic lattice-plane separations indicated in Table 2a.

The present invention furthermore relates to crystal form II of calcium 3-acetylaminopropane-1-sulfonate, which is characterised by the physical data by at least one of the analytical methods described above and below.

On investigation by means of single-crystal X-ray diffractometry, the following characteristic parameters arise for crystal form II of calcium 3-acetyl-aminopropane-1-sulfonate: triclinic, $P\bar{1}$, a=5.54 Å, b=8.15 Å, c=9.76, α=69.1°, β=84.3°, γ=89.4°, V=409.66 Å³ (Oxford Xcalibur diffractometer (Mo $K_\alpha$ rays), graphite monochromator, sapphire CCD, data evaluation using SHELX-97 software suite).

The present invention furthermore relates to crystal form II of calcium 3-acetylaminopropane-1-sulfonate, characterised by the following parameters: $P\bar{1}$, a=5.54 A, b=8.15 A, c=9.76, α=69.1°, β84.3°, γ=89.4°, V=409.66 A³.

Figure 3:
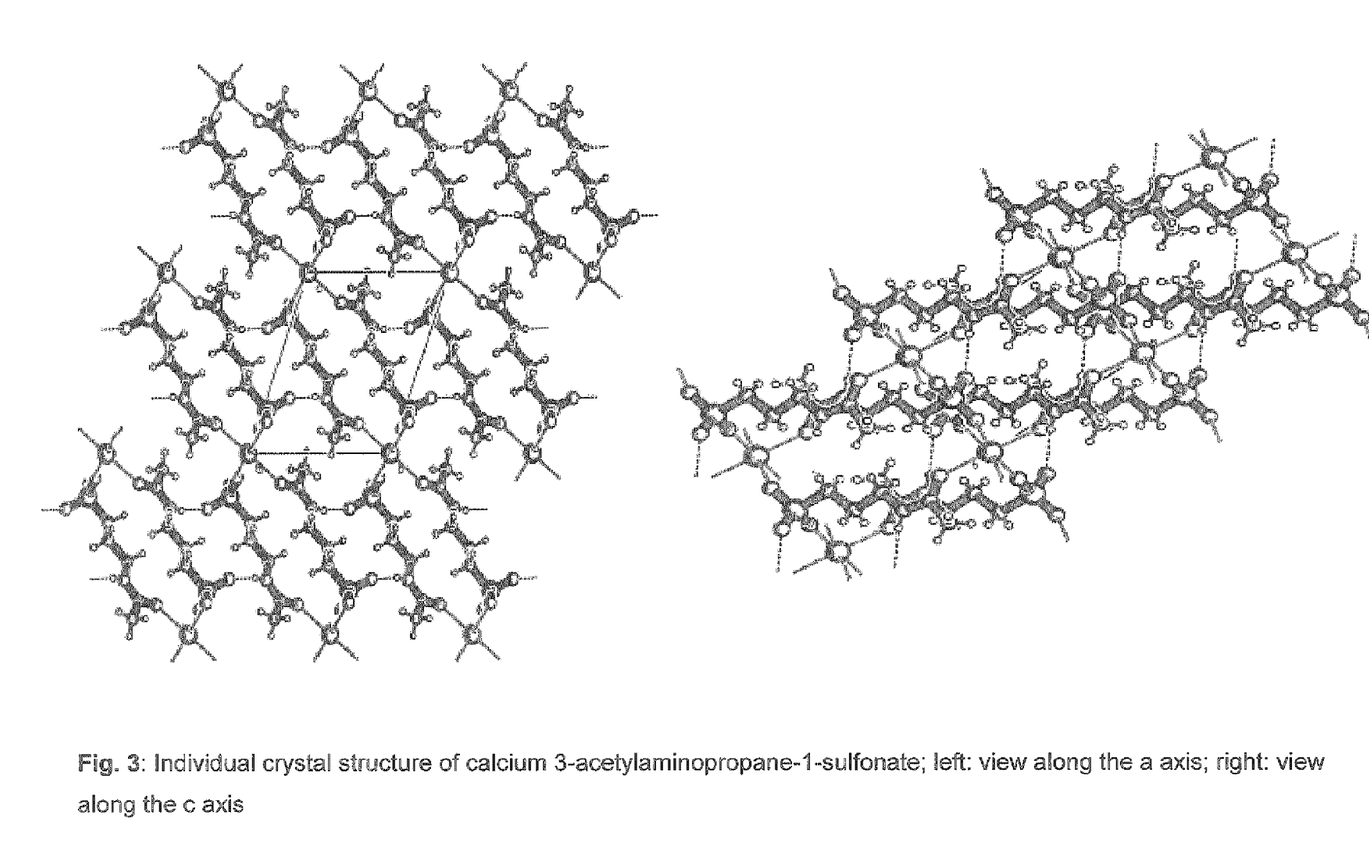
FIG. 3 illustrates the crystal structure of form II.

The crystal structure arising is depicted in FIG. 3. As is evident therefrom, the crystal structure of form II contains neither water nor another solvent.

"Form II, essentially consisting of form II" is taken to mean above and below that crystal form II comprises less than 5% by weight, preferably less than 2% by weight and particularly preferably less than one % by weight of form I.

The present invention thus furthermore relates to calcium 3-acetylamino-propane-1-sulfonate essentially consisting of crystal form II.

The invention furthermore relates to a process for the preparation of crystal form II of the active compound, which is characterised in that crystals of calcium 3-acetylaminopropane-1-sulfonate in crystal form I are stirred in a suspension medium, and the residue obtained is separated off and dried.

The active compound can of course also be employed as a mixture of its crystal forms II and I, where in each case more than 10% by weight, 20% by weight, 30% by weight, 40% by weight, 50% by weight, 60% by weight, 70% by weight, 80% by weight or 90% by weight of crystal form II may be present. Preference is given in accordance with the invention to mixtures comprising more than 70% by weight, particularly preferably comprising more than 80% by weight and particularly preferably comprising more than 90% by weight of crystal form II.

Crystal form II is, as already described, thermodynamically stable and therefore particularly suitable as medicament. The invention therefore also relates to crystal form II as medicament.

The invention likewise relates to a pharmaceutical composition comprising crystal form II.

The present invention furthermore relates to crystal form II for the preparation of a medicament.

The working examples, without being restricted thereto, explain the invention.

EXAMPLE 1

Preparation of Crystal Form II of Calcium 3-Acetylaminopropane-1-Sulfonate 3 g of calcium 3-acetylaminopropane-1-sulfonate are suspended in 2 ml of demineralised water and stirred at room temperature for 7 days. The suspension obtained is filtered and dried.

EXAMPLE 2

Analytical Characterisation of Crystal Form II Obtained in Accordance with Example 1

In order to characterise the crystal form of the crystals obtained in accordance with Example 1 (form II), infrared (FT-IR) and Raman spectra (FT-Raman) are recorded. FT-IR and FT-Raman are standard methods and are carried out as described in the European Pharmacopoeia, 6th Edition, Chapters 2.02.24 and 2.02.48.

Figure 4:
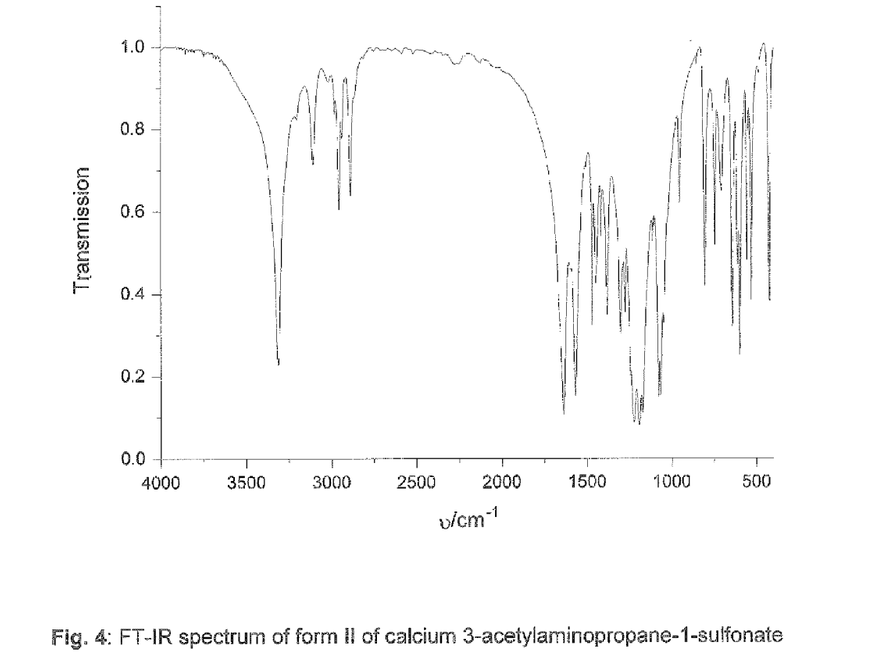
FIG. 4 shows the infrared (FT-IR) spectrum of form II.

The FT-IR spectroscopy is carried out using KBr pressed discs. The measured FT-IR spectrum is shown in FIG. 4, it has the typical bands indicated below (the wavenumbers of the IR bands ($cm^{-1\pm2}$ $cm^{-1}$) and the relative intensities thereof are indicated):
3311 $cm^{-1}$ (m), 3106 $cm^{-1}$ (m), 2955 $cm^{-1}$ (m), 2888 $cm^{-1}$ (m), 1637 $cm^{-1}$ (s), 1568 $cm^{-1}$ (s), 1470 $cm^{-1}$ (m), 1449 $cm^{-1}$ (m), 1417 $cm^{-1}$ (m), 1380 $cm^{-1}$ (m), 1302 $cm^{-1}$ (m), 1274 $cm^{-1}$ (m), 1223 $cm^{-1}$ (s), 1191 $cm^{-1}$ (s), 1172 $cm^{-1}$ (s), 1076 $cm^{-1}$ (s), 1066 $cm^{-1}$ (s), 953 $cm^{-1}$ (m), 804 $cm^{-1}$ (m), 744 $cm^{-1}$ (m), 706 $cm^{-1}$ (m), 642 $cm^{-1}$ (m), 611 $cm^{-1}$ (m), 598 $cm^{-1}$ (m), 556 $cm^{-1}$ (m), 529 $cm^{-1}$ (m), 424 $cm^{-1}$ (m).

Measurement conditions: FT-IR spectroscopy, Bruker Vector 22, 2 $cm^{-1}$ spectral resolution, 32 scans.

Evaluation: The FT-IR spectrum obtained is background-corrected (Bruker OPUS software). The bands are divided on the basis of their transmission into
s=strong (transmission≦20%),
m=moderate (20%<transmission≦60%)
w=weak (transmission>60%).

Figure 5:
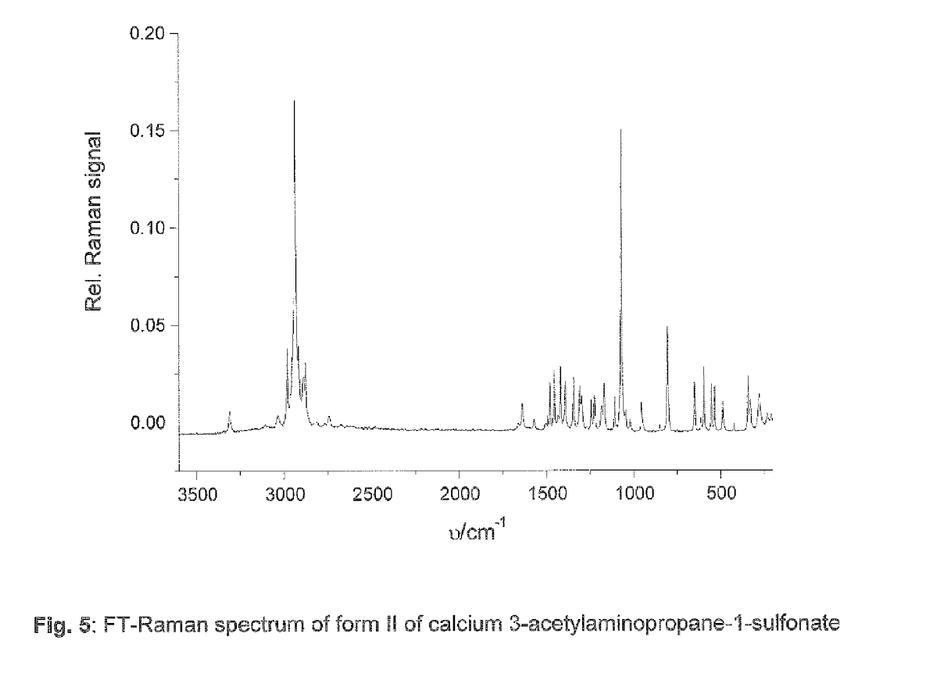
FIG. 5 shows the Raman spectra (FT-Raman) of form II.

The measured FT-Raman spectrum is depicted in FIG. 5 and has the typical bands indicated below:
3310 $cm^{-1}$ (w), 2981 $cm^{-1}$ (m), 2937 $cm^{-1}$ (s), 2877 $cm^{-1}$ (m), 1637 $cm^{-1}$ (m), 1480 $cm^{-1}$ (m), 1453 $cm^{-1}$ (m), 1419 $cm^{-1}$ (m), 1392 $cm^{-1}$ (m), 1345 $cm^{-1}$ (m), 1310 $cm^{-1}$ (m), 1300 $cm^{-1}$ (w), 1244 $cm^{-1}$ (w), 1226 $cm^{-1}$ (m), 1169 $cm^{-1}$ (m), 1109 $cm^{-1}$ (m), 1070 $cm^{-1}$ (s), 955 $cm^{-1}$ (m), 805 $cm^{-1}$ (m), 649 $cm^{-1}$ (m), 595 $cm^{-1}$ (m), 553 $cm^{-1}$ (m), 534 $cm^{-1}$ (m), 487 $cm^{-1}$ (m).

Wavenumbers of the Raman bands ($cm^{-1\pm2}$ $cm^{-1}$) and the relative intensities thereof.

Measurement conditions: FT-Raman spectroscopy, Bruker RFS 100, 1064 nm excitation, 500 mW, 1 $cm^{-1}$ spectral resolution, 500 scans.

Evaluation: The Raman spectrum obtained is vector-standardised in the spectral range 3600-250 $cm^{-1}$. The bands are divided on the basis of their intensity into
s=strong (rel. Raman intensity≧0.1)
m=moderate (0.1<rel. Raman intensity≧0.025)
w=weak (rel. Raman intensity<0.025).

EXAMPLE 3

Analytical Characterisation of Form I

For comparative purposes, form I of the active compound (starting material of Example 1) is analytically characterised and evaluated analogously to Example 2.

Figure 6:
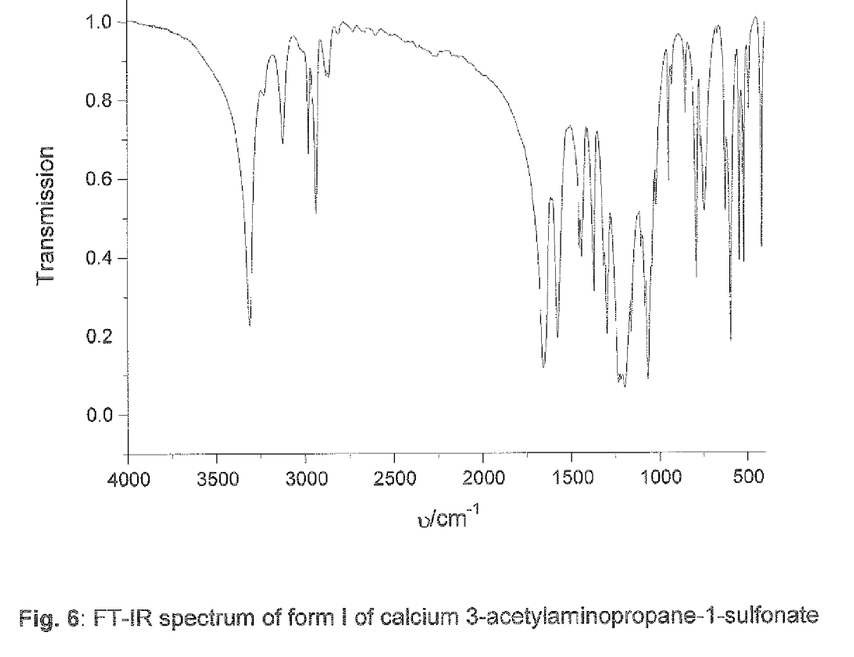
FIG. 6 shows the infrared (FT-IR) spectrum of form I.

The FT-IR spectrum of form 1 is depicted in FIG. 6, this has the following parameters:
3312 $cm^{-1}$ (m), 3123 $cm^{-1}$ (w), 2980 $cm^{-1}$ (w), 2937 $cm^{-1}$ (m), 2878 $cm^{-1}$ (w), 2864 $cm^{-1}$ (w), 1658 $cm^{-1}$ (s), 1577 $cm^{-1}$ (s), 1453 $cm^{-1}$ (m), 1441 $cm^{-1}$ (m), 1370 $cm^{-1}$ (m), 1298 $cm^{-1}$ (s), 1234 $cm^{-1}$ (s), 1219 $cm^{-1}$ (s), 1199 $cm^{-1}$ (s), 1160 $cm^{-1}$ (s), 1083 $cm^{-1}$ (m), 1064 $cm^{-1}$ (s), 1018 $cm^{-1}$ (m), 946 $cm^{-1}$ (m), 850 $cm^{-1}$ (w), 789 $cm^{-1}$ (iii), 744 $cm^{-1}$ (m), 625 $cm^{-1}$ (m), 596 $cm^{-1}$ (s), 545 $cm^{-1}$ (m), 521 $cm^{-1}$ (m), 490 $cm^{-1}$ (w), 418 $cm^{-1}$ (m).

Figure 7:
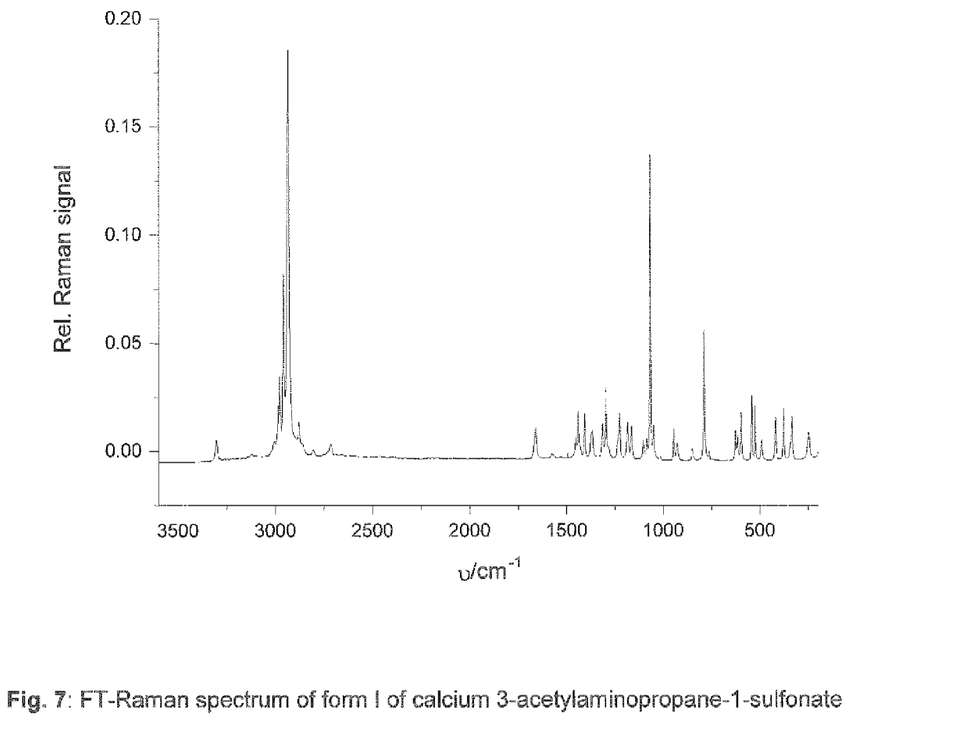
FIG. 7 shows the Raman spectra (FT-Raman) of form I.

The FT-Raman spectrum of form 1 is depicted in FIG. 7, it is characterised by the following parameters:
3304 $cm^{-1}$ (w), 2980 $cm^{-1}$ (m), 2958 $cm^{-1}$ (m), 2934 $cm^{-1}$ (s), 2879 $cm^{-1}$ (w), 1661 $cm^{-1}$ (m), 1454 $cm^{-1}$ (m), 1442 $cm^{-1}$ (w), 1408 $cm^{-1}$ (w), 1369 $cm^{-1}$ (w), 1316 $cm^{-1}$ (w), 1298 $cm^{-1}$ (m), 1227 $cm^{-1}$ (w), 1187 $cm^{-1}$ (w), 1165 $cm^{-1}$ (w), 1103 $cm^{-1}$ (w), 1084 $cm^{-1}$ (w), 1068 $cm^{-1}$ (s), 1051 $cm^{-1}$ (w), 946 $cm^{-1}$ (w), 929 $cm^{-1}$ (w), 790 $cm^{-1}$ (m), 627 $cm^{-1}$ (w), 616 $cm^{-1}$ (w), 598 $cm^{-1}$ (w), 542 $cm^{-1}$ (m), 524 $cm^{-1}$ (m), 490 $cm^{-1}$ (w).

The invention claimed is:

1. The crystal form II of calcium 3-acetylaminopropane-1-sulfonate, characterised by the following characteristic lattice-plane separations in Å:

| No. | d [Å] | 2Θ ± 0.1 |
| --- | --- | --- |
| 1 | 7.59 | 11.6 |
| 2 | 4.51 | 19.7 |
| 3 | 4.26 | 20.8 |
| 4 | 3.80 | 23.4 |
| 5 | 3.74 | 23.8 |
| 6 | 3.61 | 24.6 |
| 7 | 3.13 | 28.5. |

2. The crystal form II of calcium 3-acetylaminopropane-1-sulfonate, characterised by the following characteristic lattice-plane separations in Å:

| No. | d [Å] | 2Θ ± 0.1 |
| --- | --- | --- |
| 1 | 9.04 | 9.8 |
| 2 | 7.59 | 11.6 |
| 3 | 5.01 | 17.7 |
| 4 | 4.51 | 19.7 |
| 5 | 4.40 | 20.2 |
| 6 | 4.26 | 20.8 |
| 7 | 3.80 | 23.4 |
| 8 | 3.74 | 23.8 |
| 9 | 3.61 | 24.6 |
| 10 | 3.42 | 26.0 |
| 11 | 3.33 | 26.7 |
| 12 | 3.13 | 28.5 |
| 13 | 2.24 | 40.2. |

3. Calcium 3-acetylaminopropane-1-sulfonate comprising crystal form II according to claim 1.

4. Calcium 3-acetylaminopropane-1-sulfonate consisting essentially of crystal form II according to claim 1.

5. A process for the preparation of crystal form II according to claim 1, said process comprising:
stirring crystals of calcium 3-acetylaminopropane-1-sulfonate in crystal form I in a suspension medium, and separating off the residue obtained and drying the obtained residue.

6. Crystal form according to claim 1 as medicament.

7. A pharmaceutical composition comprising crystal form II according to claim 1 and one or more assistants.

8. Calcium 3-acetylaminopropane-1-sulfonate comprising crystal form II according to claim 2.

9. Calcium 3-acetylaminopropane-1-sulfonate consisting essentially of crystal form II according to claim 3.

10. A process for the preparation of crystal form II according to claim 2, said process comprising:
stirring crystals of calcium 3-acetylaminopropane-1-sulfonate in crystal form I are in a suspension medium, and separating off the residue obtained and drying the obtained residue.

11. A pharmaceutical composition comprising crystal form II according to claim 2 and one or more assistants.

12. A method for the treatment of alcoholism or tinnitus, comprising administering an effective amount of crystal form II according to claim 1.

13. A method for the treatment of alcoholism or tinnitus, comprising administering an effective amount of crystal form II according to claim 2.

14. Crystal form II of calcium 3-acetylaminopropane-1-sulfonate, characterised by one or more of the following characteristic lattice-plane separations in Å:

| No. | d [Å] | 2Θ ± 0.1 |
|-----|-------|----------|
| 3   | 4.26  | 20.8     |
| 4   | 3.80  | 23.4     |
| 5   | 3.74  | 23.8     |
| 6   | 3.61  | 24.6     |
| 7   | 3.13  | 28.5.    |

15. The crystal form II of calcium 3-acetylaminopropane-1-sulfonate, characterised by an FT-IR spectrum having the following IR bands, wherein the wavenumbers of the IR bands are ±2 cm$^{-1}$:

3311 cm$^{-1}$ (m), 3106 cm$^{-1}$ (m), 2955 cm$^{-1}$ (m), 2888 cm$^{-1}$ (m), 1637 cm$^{-1}$ (s), 1568 cm$^{-1}$ (s), 1470 cm$^{-1}$ (m), 1449 cm$^{-1}$ (m), 1417 cm$^{-1}$ (m), 1380 cm$^{-1}$ (m), 1302 cm$^{-1}$ (m), 1274 cm$^{-1}$ (m), 1223 cm$^{-1}$ (s), 1191 cm$^{-1}$ (s), 1172 cm$^{-1}$ (s), 1076 cm$^{-1}$ (s), 1066 cm$^{-1}$ (s), 953 cm$^{-1}$ (m), 804 cm$^{-1}$ (m), 744 cm$^{-1}$ (m), 706 cm$^{-1}$ (m), 642 cm$^{-1}$ (m), 611 cm$^{-1}$ (m), 598 cm$^{-1}$ (m), 556 cm$^{-1}$ (m), 529 cm$^{-1}$ (m), 424 cm$^{-1}$ (m).

16. The crystal form II of calcium 3-acetylaminopropane-1-sulfonate, characterised by an FT-Raman spectrum having the following Raman bands wherein the wavenumbers of the Raman bands are ±2 cm$^{-1}$:

3310 cm$^{-1}$ (w), 2981 cm$^{-1}$ (m), 2937 cm$^{-1}$ (s), 2877 cm$^{-1}$ (m), 1637 cm$^{-1}$ (m), 1480 cm$^{-1}$ (m), 1453 cm$^{-1}$ (m), 1419 cm$^{-1}$ (m), 1392 cm$^{-1}$ (m), 1345 cm$^{-1}$ (m), 1310 cm$^{-1}$ (m), 1300 cm$^{-1}$ (w), 1244 cm$^{-1}$ (w), 1226 cm$^{-1}$ (m), 1169 cm$^{-1}$ (m), 1109 cm$^{-1}$ (m), 1070 cm$^{-1}$ (s), 955 cm$^{-1}$ (m), 805 cm$^{-1}$ (m), 649 cm$^{-1}$ (m), 595 cm$^{-1}$ (m), 553 cm$^{-1}$ (m), 534 cm$^{-1}$ (m), 487 cm$^{-1}$ (m).

17. A method according to claim 12, wherein said method is for the treatment of alcoholism.

18. A method according to claim 12, wherein said method is for the treatment of tinnitus.

* * * * *